United States Patent
Yan et al.

(10) Patent No.: US 6,776,792 B1
(45) Date of Patent: Aug. 17, 2004

(54) COATED ENDOVASCULAR STENT

(75) Inventors: John Y. Yan, Los Gatos, CA (US); Randy Chan, San Jose, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 594 days.

(21) Appl. No.: 08/847,763

(22) Filed: Apr. 24, 1997

(51) Int. Cl.$^7$ .................................................. A61F 2/06
(52) U.S. Cl. .................... 623/1.15; 623/1.43; 623/1.46; 427/2.25
(58) Field of Search .............................. 623/1, 12, 1.43, 623/1.42, 1.46, 23.71, 1.15; 606/191, 198, 108; 427/2.25

(56) References Cited

U.S. PATENT DOCUMENTS

| | | |
|---|---|---|
| 3,288,728 A | 11/1966 | Gorham |
| 3,839,743 A | 10/1974 | Schwarcz |
| 4,164,524 A * | 8/1979 | Ward et al. .................... 264/39 |
| 4,346,028 A | 8/1982 | Griffith |
| 4,633,873 A | 1/1987 | Dumican et al. |
| 4,656,083 A | 4/1987 | Hoffman et al. |
| 4,699,611 A | 10/1987 | Bowden |
| 4,718,907 A | 1/1988 | Karwoski et al. |
| 4,722,335 A | 2/1988 | Vilasi |
| 4,723,549 A | 2/1988 | Wholey et al. |
| 4,816,339 A | 3/1989 | Tu et al. |
| 4,828,561 A * | 5/1989 | Woodroof ..................... 623/8 |
| 4,865,870 A * | 9/1989 | Hu et al. .................... 427/2.25 |
| 4,877,030 A | 10/1989 | Beck et al. |
| 4,879,135 A | 11/1989 | Greco et al. |
| 4,943,346 A | 7/1990 | Mattelin |
| 4,994,298 A | 2/1991 | Yasuda |
| 5,047,050 A | 9/1991 | Arpesani |
| 5,053,048 A | 10/1991 | Pinchuk |
| 5,085,629 A | 2/1992 | Goldberg et al. |

(List continued on next page.)

FOREIGN PATENT DOCUMENTS

| | | |
|---|---|---|
| CA | 2008312 | 7/1990 |
| CA | 2007648 | 4/1991 |
| CA | 1322628 | 10/1993 |
| CA | 1336319 | 7/1995 |
| CA | 1338303 | 5/1996 |
| EP | 0380 668 A1 | 4/1989 |
| EP | 0 351 314 | 1/1990 |
| EP | 0517 075 A1 | 12/1992 |
| EP | 0 540 290 A2 | 5/1993 |
| EP | 0 565 251 A1 | 10/1993 |

(List continued on next page.)

OTHER PUBLICATIONS

J. R. Hollahan et al., Attachment of Amino Groups to Polymer Surfaces by Radiofrequency Plasmas, Journal of Applied Polymer Science, vol. 13, pp. 807–816 (1969).
N. Inagaki et al., Hydrophilic Surface Modification of Polyethylene by No–Plasma Treatment, Adhesion Sci.Technol., vol. 4, No. 2, pp. 99–107 (1990).
Carl–Gustaf Gölander et al., RF–Plasma–Modified Polystyrene Surfaces for Studying Complement Activation, J. Biomater. Sci. Plymer Edn, vol. 4, No. 1, pp. 25–30 (1992).

(List continued on next page.)

*Primary Examiner*—Paul B. Prebilic
(74) *Attorney, Agent, or Firm*—Squire, Sanders & Dempsey

(57) ABSTRACT

An implantable stent is coated with a material that attracts heparin and with which heparin forms a bond. The stent is exposed to a heparin containing solution just prior to implantation or is first implanted and then exposed to heparinized blood. As heparin becomes detached from the stent, the implantation site is exposed to heparin to restore an effective level and thereby prevent thrombosis.

12 Claims, 1 Drawing Sheet

U.S. PATENT DOCUMENTS

| | | | |
|---|---|---|---|
| 5,108,755 A | | 4/1992 | Daniels et al. |
| 5,116,365 A | | 5/1992 | Hillstead |
| 5,134,192 A | * | 7/1992 | Feijen et al. ............... 525/54.1 |
| 5,156,623 A | | 10/1992 | Hakamatsuka et al. |
| 5,192,311 A | | 3/1993 | King et al. |
| 5,197,977 A | | 3/1993 | Hoffman, Jr. et al. |
| 5,222,971 A | | 6/1993 | Willard et al. |
| 5,226,913 A | | 7/1993 | Pinchuk |
| 5,234,456 A | | 8/1993 | Silvestrini |
| 5,234,457 A | | 8/1993 | Andersen |
| 5,236,447 A | | 8/1993 | Kubo et al. |
| 5,269,802 A | | 12/1993 | Garber |
| 5,279,594 A | | 1/1994 | Jackson |
| 5,282,823 A | | 2/1994 | Schwartz et al. |
| 5,282,860 A | | 2/1994 | Matsuno et al. |
| 5,289,831 A | | 3/1994 | Bosley |
| 5,290,271 A | | 3/1994 | Jernberg |
| 5,304,200 A | | 4/1994 | Spaulding |
| 5,306,286 A | | 4/1994 | Stack et al. |
| 5,314,472 A | | 5/1994 | Fontaine |
| 5,330,500 A | | 7/1994 | Song |
| 5,342,348 A | | 8/1994 | Kaplan |
| 5,342,621 A | | 8/1994 | Eury |
| 5,356,433 A | | 10/1994 | Rowland et al. |
| 5,360,443 A | | 11/1994 | Barone et al. |
| 5,364,354 A | | 11/1994 | Walker et al. |
| 5,370,684 A | | 12/1994 | Vallana et al. |
| 5,383,927 A | | 1/1995 | DeGoicoechea et al. |
| 5,389,106 A | | 2/1995 | Tower |
| 5,423,849 A | | 6/1995 | Engelson et al. |
| 5,455,040 A | * | 10/1995 | Marchant ................... 424/426 |
| 5,464,650 A | * | 11/1995 | Berg et al. ................... 427/2.3 |
| 5,562,728 A | | 10/1996 | Lazarus et al. |
| 5,571,166 A | | 11/1996 | Dinh et al. |
| 5,588,962 A | * | 12/1996 | Nicholas et al. .............. 604/52 |
| 5,609,629 A | | 3/1997 | Fearnot et al. |
| 5,618,298 A | | 4/1997 | Simon |
| 5,624,411 A | | 4/1997 | Tuch |
| 5,628,755 A | | 5/1997 | Heller et al. |
| 5,628,781 A | | 5/1997 | Williams et al. |
| 5,637,113 A | | 6/1997 | Tartaglia et al. |
| 5,718,726 A | * | 2/1998 | Amon et al. ................... 623/11 |
| 5,804,318 A | * | 9/1998 | Pinchuk et al. ............. 428/421 |
| 5,824,048 A | * | 10/1998 | Tuch .............................. 623/1 |
| 5,997,517 A | * | 12/1999 | Whitbourne ................ 604/265 |
| 6,120,535 A | * | 9/2000 | McDonald et al. ........ 623/1.39 |

FOREIGN PATENT DOCUMENTS

| | | |
|---|---|---|
| EP | A-0 604 022 | 1/1994 |
| EP | A-0 578 998 | 6/1994 |
| EP | A-0 621 017 | 10/1994 |
| EP | 0 649 637 A | 4/1995 |
| EP | 0 701 802 A | 3/1996 |
| EP | 0 716 836 A | 6/1996 |
| EP | 0 832 618 | 9/1996 |
| EP | 0 756 853 A | 2/1997 |
| JP | SHO49-48336 | 12/1974 |
| JP | SHO54-18317 | 7/1979 |
| JP | SHO60-28504 | 7/1985 |
| JP | HEI6-38851 | 5/1994 |
| JP | HEI8-33718 | 2/1996 |
| JP | HEI10-151190 | 6/1998 |
| WO | WO 91/17789 | 11/1991 |
| WO | WO 93/06792 | 4/1993 |
| WO | WO 95/11817 | 5/1995 |
| WO | WO 96/28115 | 9/1996 |
| WO | WO 97/10011 A | 3/1997 |

OTHER PUBLICATIONS

Fabienne Poncin–Epaillard et al., Reactivity of a Polypropylene Surface Modified in a Nitrogen Plasma, Plasma Surface Modification of Polymers, pp. 167–180 (1994).

Thomas R. Gengenbach et al., Evolution of the Surface Composition and Topography of Perfluorinated Polymers Following Ammonia–Plasma Treatment, Plasma Surface Modification of Polymers, pp. 123–146 (1994).

U.S. patent application Ser. No. 08/233,046 filed Aug. 25, 1994.

Lambert, Thomas L. M.D., et al., Localized Arterial Wall Drug Delivery From a Polymer–Coated Removable Metallic Stent, Circulation, Eol. 90, No. 2 (Aug. 1994) pp. 1003–1011.

De Scheerder, Ivan K, et al., Biocompatibility of Polymer–Coated Oversized Stents Implanted in Normal Porcine Coronary Arteries, *Atherosclerosis,* vol. 114 (1995) pp. 105–114.

U.S. patent application Ser. No. 08/564,936 (FWC of 08/233,046) filed Apr. 28, 1995.

U.S. patent application Ser. No. 08/234,547 filed Aug. 1994.

U.S. patent application Ser. No. 08/559,931 (FWC of 08/234,547) filed Nov. 17, 1995.

U.S. patent application Ser. No. 08/156,268 filed Nov. 22, 1993.

Union Carbide Technology Letter, New Business Department—Parylene, Oct. 1973, No. 7 (8 pages).

Union Carbide, Electronic Materials, Parylene Products, Oct. 1973, No. 9 (23 pages).

Union Carbide, Technology Letter, May 1974, No. 11 (12 pages).

Union Carbide Technology Letter, Oct. 1975, No. 15 (13 pages).

Union Carbide, Electronic Materials, Parylene Products, Mar. 1976, No. 16 (4 pages).

Eskin, et al., Growth of Cultured Calf Aortic Smooth Muscle Cells on Cardiovascular Prosthetic Materials, J. Biomed. Mater. Res. vol. 10, pp 113–122 (1976).

Loeb, et al., Parylene as a Chronically Stable, Reproducible Microelectrode Insulator, IEEE Transactions on Biomedical Engineering, Mar. 1977, (pp. 121–128).

Union Carbide, Electronic Materials, Parylene Products, Aug. 1977, No. 18 (7 pages).

Union Carbide, Electronic Materials, Parylene Prodcuts, Oct. 1977, No. 1 Revision 2 (7 pages).

Union Carbide, Electronic Materials, Parylene Products, Oct. 1977, No. 2 Revision 1 (9 pages).

Union Carbide, Electronic Materials, Parylene Products, Oct. 1977, No. 3 (21 pages).

Union Carbide, Electronics Materials, Parylene Products, Oct. 1977, No. 4 (13 pages).

Union Carbide, Electronic Materials, Parylene Products, Oct. 1977, No. 6 (12 pages).

Union Carbide, Electronic Materials, Parylene Products, Oct. 1977, No. 7 Revision 1 (8 pages).

Union Carbide, Electronic Materials, Parylene Products, Oct. 1977, No. 8, Edited (19 pages).

Union Carbide, Electronic Materials, Parylene Products, Oct. 1977, No. 10 (50 pages).

Union Carbide, Electronic Materials, Parylene Products, Oct. 1977, No. 11 (12 pages).

Union Carbide, Electronic Materials, Parylene Products, Oct. 1977, No. 12, Revision 1 (6 pages).

Union Carbide, Electronic Materials, Parylene Products, Oct. 1977, No. 13, Revision 1 (7 pages).

Union Carbide, Electronic Materials, Parylene Products, Oct. 1977, No. 14, Revision 1 (11 pages).

Union Carbide, Electronic Materials, Parylene Products, Oct. 1977, No. 15, Revision 1 (8 pages).

Union Carbide, Electronics Materials, Parylene Products, Oct. 1977, No. 17, Revision 1 (11 pages).

ISEEE Transactions on Biomedical Engineering, vol. BME–27, No. 11, Nov. 1980 (5 pages).

Sadhir, et al., The Adhesion of Glow–Discharge Polymers, Silastic and Parylene to Implantable Platinum Electrodes: Results of Tensile Pull Tests After Exposure to Isotonic Sodium Chloride, Oct. 1981, vol. 2, Biomaterials (pp. 239–243).

Hahn, et al., Glow Discharge Polymers as Coatings for Implanted Devices, John M. Dlaton Research Center, University of Missouri–Columbia and the Graduate Center for Materials REsearch, 1981 (pp. 109–113).

Union Arbide, Electrode Materials, Parylene Products, Jan. 18, 1982, No. 5, Revision 4 (17 pages).

Hahn, et al., Biocompatibility of Glow–Discharge–Polymerized Films and Vacuum–Deposited Parylene, Journal of Applied Polymer Science: Applied Polymer Symposium 38, 55–64 (1984).

Casper, et al., Fiber–Reinforced Absorbable Compsite for Orthopedic Surgery, *Polymeric Materials Science and Engineering,* Proceedings of the ACS Division of Polymeric Materials: Science and Engineering, vol. 53, Fall Meeting 1985.

Kelly et al., Totally Resorbable High–Strength Composite Mateiral, *Advances in Biomedical Polymers,* Edited by Charles G. Gebelein (1987).

Yuen, et al., Tissue Response to Potential Neuroprosthetic Materials Implanted Subdurally, Biomaterials, Mar. 1987, vol. 8, (pp. 57–62).

Nichols, et al., Electrical Insulation of Implantable Devices by Composite Polymer Coatings, Dalton Research Center, University of Missouri, 1987.

Schmidt, et al., Long–Term Implants of Parylene–C Coated Microelectrodes, Medical & Biological Engineering & Computing, Jan. 1988 (pp. 96–101).

Olson, Parylene, a Biostable Coating for Medical Applications, for NOVA TRAN Parylene Coating Services (Jul. 25, 1988; Nov. 14, 1988).

Beach, et al., Xylylene Polymers, Encyclopedia of Polymer Science and Engineering, vol. 17, Second Edition, pp. 990–1025, 1989.

Muller, et al., Advances in Coronary Angioplasty: Endovascular stents, *Coronary Artery Disease,* Jul./Aug. 1990, vol. 1, No. 4.

Loh, et al., Plasma Enhanced Parylene Deposition, Antec, pp. 1099–1103, 1991.

Gebelein, et al., Biomedical and Dental Applications of Polymers, Polymer Science and Technology, vol. 14 (No. date)(pp. 143–161).

Wong, M.D., et al., An Update on Coronary Stents, *Cardio,* Feb. 1992.

The Parylene Press (A Publication of Specialty Coating Systems, Inc.), Winter 1992 (7 pages).

Charlson, et al., Temperature Selective Deposition of Parylene–C, IEEE Transactions on Biomedical Engineering, vol. 39, No. 2, Feb. 1992 (pp. 202–206).

Bull: Parylene Coating for Medical Applications, Medical Product Manufacturing News, Mar. 1993 (2 pages).

The Parylene Press (A Publication of Specialty Coating Systems, Inc.), Spring 1993 (6 pages).

The Parylene Press (A Publication of Specialty Coating Systems, Inc.), Summer 1993 (4 pages).

Information Regarding Parylene–C Coating for ACS Metal Stent, In–Home Memorandum from Ed Newton to Joe Callol, Mike Clayman, Dennis Houlsby and Joe Tartaglia, Oct. 15, 1993 attaching Parylene, a Biostable Coating for Medical Application by Roger Olson.

Moody: Vacuum Coating Ultrasonic Transducers, Sensors, Dec. 1993 (1 page).

Union Carbide A–174 Silane, Sales Brochure, Union Carbide Adhesion Promoters, Jan. 1968 (5 pages).

Parylene Conformal Coatings Speficiations and Properties, Sales Brochure, Union Carbide Specialty Coating Systems (12 pages).

Parylene Environmentally Compatible Conformal Coatings for Electronic Components Assemblies and Precision Parts, Brochure, Union Carbide Electronics Division (14 pages).

Parylene and Nova Tran™ Parylene Coating Services, for Unmatched Conformal Coating Performance, Brochure, Union Carbide Specialty Coating Systems (21 pages).

Repair and Recoating of Parylene Coated Printed Circuit Boards, Brochure, Union Carbide Specialty Coating Systems (15 pages).

Nova Tan™ Custom Coating Services, Parylene Conformal Coating, Brochure, Union Carbide (8 pages).

Parylene, a Biostable Coating for Medical Applications, Brochure, Union Carbide Specialty Coating Systems (6 pages).

Typical Parylene Properties, Printout, Para Tech Coating Company; Lab Top® Parylene Deposition System Model 3000, Sales Brochure, Para Tech Coating Company (7 pages).

* cited by examiner

COATED ENDOVASCULAR STENT

BACKGROUND OF THE INVENTION

The present invention relates to endovascular stents and more particularly pertains to coatings that are applied to stents in order to reduce thrombogenicity.

Stents are implanted within blood vessels in an effort to maintain their patency by preventing collapse of the lumen and/or by impeding restenosis. Unfortunately, the presence of a foreign object within the blood flow may have a thrombogenic effect. It has therefore been found to be desirable to use various anti-coagulant drugs in an effort to reduce the likelihood of the development of restenosis and provide an antithrombogenic effect.

A drug that has been found to be particularly effective for such purpose is heparin. By maintaining an effective concentration of the drug in and about the implantation site until the stent is encapsulated by tissue, the risk of thrombogenesis is substantially mitigated. To that end, various approaches have been employed in the administration of heparin.

While the systemic administration of heparin can cause the implantation site to be subjected to an effective level of heparin, such level of heparin would necessarily also be present throughout the rest of the body which can lead to undesirable side effects such as bleeding. It has therefore been recognized that a regimen wherein the heparin is substantially constrained to the implantation site is far more desirable. An approach that has been devised to achieve such end requires the coating or impregnation of the stent itself with heparin. The heparin is thereby concentrated where it is most needed while its presence, and consequently its effect, throughout the rest of the body is minimized.

Disadvantages associated with heretofore known heparinized stents include, the limited shelf life of such devices, the fact the heparin is degraded when the stent is sterilized either by heat or by exposure to ethylene dioxide, the inability of the physician to alter the dosage that the patient is subjected to and the inability to replenish any heparin that may be lost while the device is deployed. Additionally, the cost of heretofore known heparinized stent devices has been very high as it necessarily includes the costs associated with the stringent regulatory requirements attendant a drug containing device.

The prior art has been unable to overcome these disadvantages and shortcomings and a new approach is needed to safely, effectively, and economically deliver heparin to an implantation site.

SUMMARY OF THE INVENTION

The present invention provides for the coating of an implantable endovascular device to facilitate the subsequent loading of heparin onto its surface. Such loading can be achieved in vitro just prior to implantation or preferably, in vivo after the device is in place. As a result, the device has a considerably longer shelf-life than heparin-containing devices, the need for special handling and sterilization procedures associated with heparin-containing devices is obviated, and the dosage of heparin can be readily tailored to an individual patient's needs including any adjustment that may be required after the device has been deployed. An additional advantage provided by such a device is that it is not subject to the stringent regulatory requirements associated with drug-containing devices.

More particularly, the present invention provides for the coating of stent surfaces with a material or combination of materials that are selected for their ability to adhere to the stent surface, to attract heparin and to form preferably an ionic bond therewith. The heparin is attracted by and attaches to functional groups incorporated in the coating which may include primary, secondary, and/or tertiary amines or other functionalities such as carboxyl groups.

The heparin-attracting coating may be applied so as to encapsulate the entire stent or alternatively, to cover only selected surfaces thereof. By limiting coverage to only the inner surface of the stent, i.e., the surface that is directly exposed to blood flow, a much higher level of heparin can be loaded onto the stent than would be safe if such level were in direct contact with the vessel wall. A toxic effect on the vessel wall is thereby avoided while the blood is exposed to a more effective concentration of heparin. Alternatively, it may be deemed sufficient to coat only the ends of the stent, i.e., where disturbance of flow is greatest and where thromboses are most likely to occur.

The coating may be applied by different processes such as by dipping, spraying or molding. The preferred method is by plasma deposition wherein a base layer, selected for its ability to adhere to the stent surface, is first deposited on the stent followed by the deposition of a top layer thereon that is selected for its ability to bond to the base layer and to avail the appropriate functional groups for bonding to the heparin.

These and other features and advantages of the present invention will become apparent from the following detailed description which, taken in conjunction with the accompanying drawings, illustrates by way of example the principles of the invention.

DETAILED DESCRIPTION OF THE PREFERRED EMBODIMENTS

Figure 1:
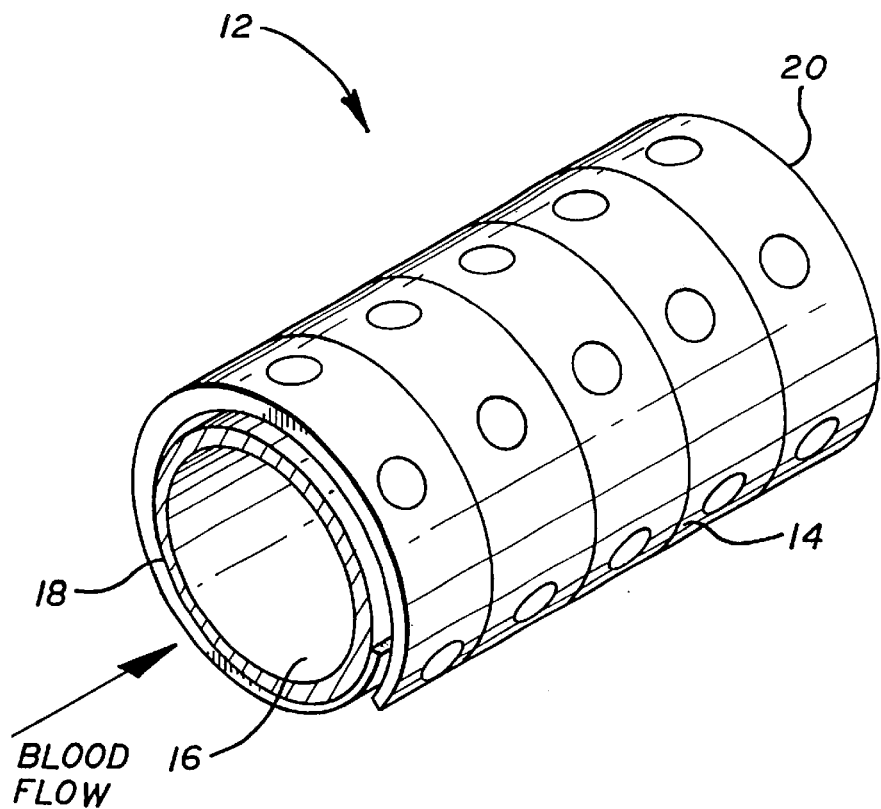
FIG. 1 is a perspective view of an implantable stent.

A wide variety of different stent configurations have been devised to address various issues inherent in their use and function. Additionally, various materials have been employed in their construction including metals and polymers. Both the degree of turbulence caused by a particular stent configuration when subjected to blood flow as well as the material from which it is constructed affects the degree of thrombogenicity associated with a particular stent device. The present invention provides a coating for such stents to which heparin becomes attached and thus serves to reduce or eliminate thrombosis formation. Moreover, the stent's coating allows the heparin to be loaded thereon immediately before the implantation procedure or after the stent is in place.

Critical requirements for the coating of the present invention include that it adheres to the stent surface and that it has functional groups that attract heparin and to which heparin bonds. Functional groups that are known to have the requisite affinity for heparin include primary, secondary, and tertiary amines wherein primary amines are preferred due to their enhanced affinity. Alternatively, carboxyl groups may be used. The functional groups must include positively charged entities that serve to attract the negatively charged entities associated with the heparin. Such attraction facilitates the formation of an ionic bond.

The coating can be applied by different processes such as by dipping, spraying, molding or by plasma deposition. Plasma deposition is preferred and first requires the deposition of a base layer or primer that prepares the surface of the stent to receive the functionality group containing substance. In the preferred embodiment, a metallic stent is first plasma deposited with methane gas leaving a film on the surface of the stent wherein the methane molecules are oriented with the carbon against the stent and the hydrogen exposed. A top layer that includes the desired functionalities is then deposited on the base layer. Such second layer may be formed by the plasma deposition of ammonia gas to leave the primary amine functional groups extending from the stent surface. Other chemicals such as alkylamine, nitrile compounds or amine containing monomers can also be used to plasma deposit amine functionalities on the surface. In the event a mixture of primary, secondary, and tertiary amines is deposited by such methods it is preferred that the primary amine constitutes a greater percentage of the mixture due to its greater affinity for heparin. Alternatively, the deposition of carboxyl functional groups can be achieved by the plasma deposition of monomers like methyl methacrylate or acrylic acid.

The resulting coating thickness should be 0.001 inch or less while a thickness less than 1 micron is preferred. Although it may be desirable to have a uniform concentration of functional groups extending from the surface, it is not critical to the function of the coating. On the other hand, a concentration of at least 54 picamoles/stent must be achieved in order to ensure that heparin becomes attached at an effective level.

The coating may be applied to the entire stent or just to selected surfaces thereon. FIG. 1 generally illustrates a stent 12 in its deployed state and serves to identify the vessel wall-facing surface 14, the blood flow-facing surface 16, its upstream edge 18, and its downstream edge 20. By coating only the surfaces facing the blood flow, a concentration of heparin can be loaded thereon that would be toxic to the vessel wall tissue if it were to be present on the surfaces in direct contact with the vessel wall. Alternatively, it may be sufficient to exclusively coat the upstream and/or downstream edges of the stent for a particular stent configuration implanted in a particular patient as thrombosis is most likely to occur at such interfaces due to turbulence induced by their presence in the blood flow.

After the coating process is completed, the coated stent is cleaned and sterilized and appropriately packaged for long-term storage. Due to the absence of any degradable drugs or substances on the stent, a fairly extended shelf-life can be expected.

Figure 2:
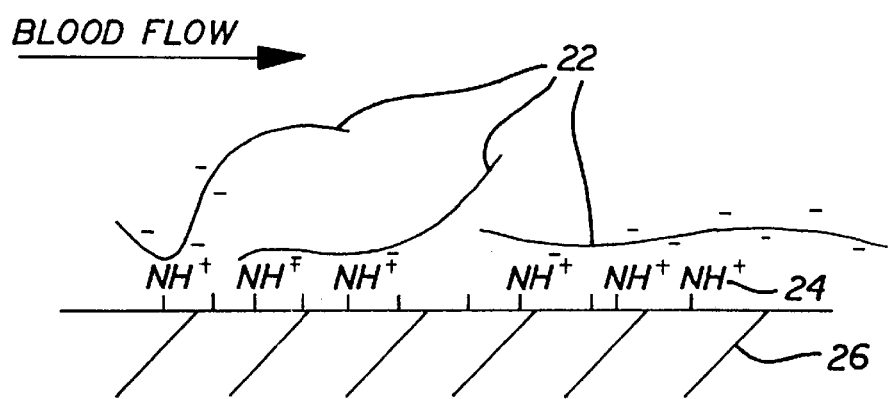
FIG. 2 is a greatly enlarged, schematic, cross-sectional view of a portion of the stent of the present invention.

The stent of the present invention can be used in two different ways. A first use calls for the stent to be implanted in the form in which it had been stored, without having heparin loaded thereon. Once in place, it is contacted with heparinized blood, either by an injection of heparin via a catheter extended to a position just upstream of the implantation site or by IV. As the heparin macromolecules 22 pass by the functional groups 24 in the coating 26, the heparin is attracted thereto and becomes attached (FIG. 2). Heparin that does not attach, quickly becomes diluted downstream of the implantation site to levels that do not adversely affect the patient. Subsequent heparin flow past the implantation site can cause more and more heparin molecules to be pulled from the blood flow until the stent coating is saturated. Once attached, heparin can inhibit coagulation by binding with anti-thrombin III and/or other factors of the coagulation cascade. Should a heparin molecule become detached, it is replaced by other heparin molecules still present in the blood flow. Alternatively, an additional dosage of heparin can be administered.

Alternatively, the physician may pre-treat the stent prior to implantation by flushing it with, for example, a heparinized saline solution. In this way, the physician can easily and precisely adjust the heparin level by controlling the concentration of the heparin in the saline solution and/or controlling the exposure time thereto. Once implanted, the heparin level can be increased or replenished by introducing heparin into the blood flow upstream of the implantation site as was described above. The heparin level is maintained on the stent until the natural healing processes cause the stent surfaces to be completely covered by tissue at which point thrombogenicity ceases to be of concern.

While a particular form of the invention has been illustrated and described, it will also be apparent to those skilled in the art that various modifications can be made without departing from the spirit and scope of the invention. Accordingly, it is not intended that the invention be limited except by the appended claims.

What is claimed is:

1. A device, comprising:
   a body that is implantable within a lumen of the vascular system, such lumen being defined by vessel walls and wherein said body has surfaces capable of contacting said vessel walls and surfaces incapable of contacting said vessel walls upon implantation; and
   a coating devoid of heparin exclusively deposited on surfaces of said body that are incapable of contacting said vessel walls wherein such coating is formed of material that adheres to said body and includes function groups to attract heparin and form a bond therewith when such material is exposed to a solution containing heparin
   whereby a toxic effect to the patient's vasculature is avoided.

2. The device of claim 1, wherein said functional groups of said coating deposited on surfaces of said body incapable of contacting said vessel walls attract heparin and form a bond when said material is exposed to a heparin-containing solution comprising heparinized blood.

3. The device of claim 1, wherein said functional groups of said coating deposited on surfaces of said body capable of contacting said vessel walls attract heparin and form a bond when said material is exposed to a heparin-containing solution comprising heparinized saline.

4. An endovascular stent, comprising:
   a support structure that is implantable within a patient's vasculature;
   a coating deposited on said support structure wherein such coating is formed of material that adheres to said stent structure and that includes functional groups to attract heparin and form an ionic bond therewith when such material is exposed to a solution containing heparin; and
   wherein said support structure is configured such that upon implantation in a blood vessel, such support structure has surfaces that face the vessel walls, surfaces that face the blood flow, and has an upstream edge and a downstream edge and wherein said coating is exclusively deposited on said surface facing said blood flow.

5. An endovascular stent, comprising:
   a support structure that is implantable within a patient's vasculature;

a coating deposited on said support structure wherein such coating is formed of material that adheres to said stent structure and includes functional groups to attract heparin and form an ionic bond therewith when such material is exposed to a solution containing heparin; and wherein said support structure is configured such that upon implantation in a blood vessel, such support structure has surfaces that face the vessel walls, surfaces that face the blood flow, and has an upstream edge and a downstream edge and wherein said coating is exclusively deposited on said edges.

6. A device comprising:

a body that is implantable within a lumen of the vascular system, such lumen being defined by vessel walls and wherein said body has surfaces capable of contacting said vessel walls and surfaces incapable of contacting said vessel walls upon implantation; and;

a coating deposited exclusively on surfaces of said body that are incapable of contacting said vessel walls, wherein such coating is formed of material that adheres to said body and includes functional groups to attract heparin and form a bond therewith when such material is exposed to a solution containing heparin; and wherein said functional groups comprise a primary amine.

7. A device, comprising:

a body that is implantable within a lumen of the vascular system, such lumen being defined by vessel walls and wherein said body has surfaces capable of contacting said vessel walls and surfaces incapable of contacting said vessel walls upon implantation; and;

a coating deposited exclusively on surfaces of said body that are incapable of contacting said vessel walls, wherein such coating is formed of material that adheres to said body and includes functional groups to attract heparin and form a bond therewith when such material is exposed to a solution containing heparin; and wherein said functional groups comprise a secondary amine.

8. The device of claim 1, wherein said functional groups comprise a teriary amine.

9. The device of claim 1, wherein said functional groups comprise carboxyl groups.

10. The device of claim 1, wherein said coating comprises a base layer, wherein such base layer is selected for its ability to adhere to said body, and a top layer, wherein such top layer is selected for its ability to bond to said base layer and includes said functional groups for bonding with heparin.

11. The device of claim 10, wherein said base layer is hydrophobically attached to said body.

12. The device of claim 10, wherein said top layer is covalently bonded to said base layer.

* * * * *